(12) United States Patent
Fielding et al.

(10) Patent No.: US 10,865,374 B2
(45) Date of Patent: Dec. 15, 2020

(54) CULTIVATION AND DISPENSING OF BACTERIA

(71) Applicant: DELAWARE CAPITAL FORMATION, INC., Wilmington, DE (US)

(72) Inventors: David Fielding, Yarm (GB); Chris Dyer, Basingstoke (GB)

(73) Assignee: Delaware Capital Formation, Inc., Wilmington, DE (US)

( * ) Notice: Subject to any disclaimer, the term of this patent is extended or adjusted under 35 U.S.C. 154(b) by 359 days.

(21) Appl. No.: 15/654,937

(22) Filed: Jul. 20, 2017

(65) Prior Publication Data

US 2017/0313969 A1 Nov. 2, 2017

Related U.S. Application Data

(62) Division of application No. 13/067,096, filed on May 6, 2011, now abandoned.

(51) Int. Cl.
*C12M 1/00* (2006.01)
*C02F 3/12* (2006.01)

(52) U.S. Cl.
CPC ........... *C12M 29/14* (2013.01); *C02F 3/1294* (2013.01)

(58) Field of Classification Search
CPC ...... C12M 23/40; C12M 27/04; C12M 27/24; C12M 29/06; C12M 29/14; A47L 15/4427; B67D 1/0045
See application file for complete search history.

(56) References Cited

U.S. PATENT DOCUMENTS

| 6,335,191 | B1 | 1/2002 | Kiplinger et al. |
| 8,409,854 | B2 * | 4/2013 | Erhardt .................. C12M 23/08 435/289.1 |
| 2005/0118702 | A1 | 6/2005 | Erhardt et al. |
| 2005/0244957 | A1 * | 11/2005 | Stock ..................... C12M 29/06 435/289.1 |
| 2006/0196816 | A1 | 9/2006 | Davis |
| 2008/0128363 | A1 | 6/2008 | Costa et al. |

FOREIGN PATENT DOCUMENTS

| FR | 2746787 | 10/1997 |
| FR | 2812628 | 8/2000 |
| WO | WO 03/012027 | * 2/2003 |

OTHER PUBLICATIONS

English Abstract of FR2812628.
English Abstract of FR2746787.

* cited by examiner

*Primary Examiner* — Thane Underdahl
(74) *Attorney, Agent, or Firm* — Dykema Gossett PLLC

(57) ABSTRACT

An apparatus 100 for cultivating bacteria, comprising a conduit 101 having an upstream and a downstream section and the downstream section of the conduit 101 comprising first Venturi eductor means 111 with at least two inlet ports 117, 118 wherein one of said inlet ports 117 is in fluid communication with a supply of nutrient and another one of said inlet ports 118 is in fluid communication with a supply of bacteria such that, in use, nutrient and bacteria are drawn into said Venturi eductor means 111 by a fluid passing along said conduit 101 and said Venturi eductor means 111.

7 Claims, 3 Drawing Sheets

CULTIVATION AND DISPENSING OF BACTERIA

The present invention relates to improvements in cultivating and dispensing bacteria, and more particularly but not exclusively to a bacteria cultivation and dispensing system for incubating bacteria from a supply population to a use population and thereafter dispensing said bacteria. A preferred use for the present invention is the removal of grease from the grease traps and plumbing of commercial kitchens such as those used in hotels, nursing homes, restaurants and the like. It will be apparent that the present invention could also be used in many other situations concerning the removal of grease, for example in the food processing industry.

Commercial kitchens generate high volumes of fats, oils and greases (FOG) and disposal of such is heavily regulated in many countries around the world. It is generally a requirement that any wastewater from a commercial kitchen contains only a small percentage of FOG by the time it enters the public sewage system. A grease trap is the most common system used to regulate these levels.

Grease traps are filters typically deployed in the plumbing between a commercial kitchen sink and the public sewer system that form a physical barrier to catch and thus filter out a high percentage of FOG residue inherent in any wastewater from a commercial kitchen sink. As a result of the high volume of wastewater that passes through these traps they need regular maintenance and cleaning to prevent any blockages occurring due to a build up of FOG deposits. Many different forms of grease trap exist but still the most common way of cleaning them is by hand, for example by using a high pressure hose or steam cleaner. Typically a commercial restaurant would employ a contractor to do this once a month.

A known alternative to such regular physical cleaning is to introduce-bacteria to the plumbing system that is capable of breaking down organic materials such as FOG. The bacteria are pumped through the plumbing and grease trap and cause the FOG residue on the walls of the plumbing and that collected by the trap to degrade into carbon dioxide and water. This can then safely pass into the public sewers. The use of such bacteria does not replace the need for regular physical cleaning but does, advantageously, greatly increase the time required between physical checks and maintenance of grease traps.

US Patent application number 2001/0051371 represents prior art in this field and discloses an automated device and method for cultivating bacteria in a fluid medium, said system typically being used to produce and supply bacteria capable of breaking down FOG and thus control grease accumulation in grease traps of commercial kitchens. The device is located upstream of a grease trap and operates automatically and at preset intervals.

A starter bacteria combined with growth stimulating nutrient is supplied in pellet form to the device. This is controllably dispensed by a hopper into a mixing chamber to be mixed with water and pressurised air. This mixing activates the bacteria such that after an incubation period it is then capable of breaking down organic materials such as FOG. At preset intervals, the activated bacteria are then flushed through the kitchen plumbing to clean said plumbing and the grease trap located downstream thereof.

The disadvantage of this device, however, is that it requires a series of control elements to manage the cultivation of active bacteria. Firstly, a control element associated with the hopper is required for regulating the dispensing of bacteria and nutrient pellets into the mixing chamber and, secondly, further control elements associated with the water and air supplies are required to manage their subsequent introduction. These control elements require regular maintenance and a constant power supply. This, in turn, adds to the running costs of the device and also introduces greater points of failure in the system.

Furthermore, US 2001/0051371 discloses a device that requires a pressurised air supply. This, again, adds to the running and maintenance costs of the device, introduces a further point of failure by adding complexity and also requires power. In addition to this, the bacteria, nutrient, water and air supply is mixed by means of continuously withdrawing and reintroducing a portion of the fluid mixture to the mixing chamber to establish a vortex therein. Such a method therefore requires a re-circulating pump that, in turn, requires a constant supply of power. Mains electricity of 110V is used to power this device.

According to the present invention, there is provided an apparatus for cultivating bacteria, comprising:
  a conduit having an upstream and a downstream section;
  the downstream section of the conduit comprising first Venturi eductor means with at least two inlet ports,
  wherein one of said inlet ports is in fluid communication with a supply of nutrient and another one of said inlet ports is in fluid communication with a supply of bacteria such that, in use, nutrient and bacteria are drawn into said Venturi eductor means by a fluid passing along said conduit and said Venturi eductor means.

A bacteria cultivation apparatus in accordance with the invention has the advantage that use of the Venturi eductor to supply nutrient and bacteria greatly simplifies said apparatus by minimising the number of powered and moving parts required and also reduces the number of conduits required to just one. This, therefore, reduces production and maintenance costs of the apparatus when compared with the prior art. Furthermore, the action of fluid flowing along the conduit draws in nutrient and bacteria thus negating the need for any additional pumps or the like. This, again, minimises production, maintenance and running costs and removes points of failure from the apparatus to make it more reliable.

Advantageously, a first valve is associated with the conduit and controls the supply of fluid therealong. The first valve is, preferably, located upstream of the first Venturi eductor means and, further advantageously, is a first timer operated valve. Preferably, the first timer operated valve is programmable to operate automatically at pre-set intervals and, advantageously, is an electrically operated solenoid valve. The solenoid valve is, preferably, battery powered.

Preferably, second Venturi eductor means is provided in fluid communication with the first and, further preferably, located downstream thereof, said Venturi eductor means having at least one inlet port. The at least one inlet port of the second Venturi eductor means is, advantageously, in fluid communication with a supply of air such that, in use, air is drawn into said second Venturi eductor means by a fluid passing therethrough. This enables the fluid, bacteria and nutrient mix to be aerated without the need for a pump or the like. This, as before, minimises production, maintenance and running costs and removes a further point of the failure from the apparatus when compared to the prior art.

The at least one inlet port of the second Venturi eductor means preferably includes a mesh filter to prevent foreign objects from entering the system. Advantageously the air supplied to the system is drawn from the atmosphere and, further advantageously, the fluid supplied is water from the mains. This negates the need for a pump to supply air to the system or the installation of a water supply in addition to the mains water supply typically present in a commercial kitchen. A supply tank may, if required, provide water to the system.

The apparatus, preferably, further comprises a mixing chamber with an inlet port, said chamber inlet port being in fluid communication with the conduit and downstream of the first Venturi eductor means, wherein, in use, the contents of the conduit flows into the mixing chamber to mix therein. In order to comply with local water regulations, an air gap, preferably, is provided between the conduit and the mixing chamber.

The mixing chamber, preferably, has an outlet port through which, the contents of the mixing chamber is dispensed to a use location. Also advantageously, the mixing chamber further includes an aerator in the form of a bubbler or the like. This stimulates the growth of active bacteria within the fluid of the mixing chamber. Further advantageously the mixing chamber includes heating means to further stimulate growth of the active bacteria.

The capacity of the mixing chamber is, preferably, between 3.5 and 6 litres and further preferably is formed by rotomoulding. Such a method of manufacture is conventional and known to those in the art.

Preferably, the apparatus further comprises means for retaining an amount of fluid in the mixing chamber such that an amount of fluid cultivated in the mixing chamber is retained in said chamber and not discharged when the fluid contained therein is dispensed. This accelerates the growth of batches of dormant bacteria subsequently added to the mix in the mixing chamber.

The amount of fluid to be retained in the mixing chamber after dispensing is, preferably, determined by a conduit or siphon added upstream of the outlet port and located inside the mixing chamber. Advantageously the conduit is an inverted U shape and has an outlet end in fluid communication with the outlet port of the mixing chamber and an inlet end positioned above said outlet end, the vertical distance between the inlet and outlet ends determining the height, and thus volume, of fluid retained in the mixing chamber after dispensing.

In a first preferred embodiment, the discharge of fluid in the mixing chamber is governed by the fluid level in said chamber rising above the apex of the inverted U shaped conduit to thus siphon up said conduit and flow out of the mixing chamber. The vertical height of the conduit from inlet end to the apex of the inverted U shape, together with the volume of the mixing chamber, thus determines the volume of fluid to be discharged.

In an alternative embodiment, the opening and closing of the outlet port of the mixing chamber is, advantageously, controlled by a second valve. Preferably, the second valve is a timer operated valve which may be programmable to operate automatically at pre-set intervals.

In either embodiment, the mixing chamber is, preferably, automatically filled with a required quantity of fluid at the beginning of a cycle and then periodically added to throughout the cycle before a discharge at the end of the cycle, for example after closing time. The apparatus is able to operate on only a minimal power supply required to control either the first or the first and second timer operated valves. Preferably, said valves are battery powered.

Advantageously, 2.5 litres of fluid are typically dispensed at once and 1 litre is retained in the mixing chamber to stimulate growth of the subsequent batch.

The second Venturi eductor means may be connected in series or in parallel with the first Venturi eductor means depending on the mixing requirements of the apparatus. It will also be apparent to the skilled reader that Venturi eductor means could comprise an eductor with one or more Venturis and or one or more inlet ports.

Preferably, the bacteria are supplied in a dormant state, suspended in a liquid and the nutrient is supplied in liquid form. Advantageously, the first Venturi eductor means draws the dormant bacteria and nutrient and, further advantageously, the rate at which dormant bacteria and nutrient is drawn through the Venturi eductor is controlled by metering tips. Also preferably, the nutrient is supplied in liquid form and tailored to cultivate the bacteria upon mixing therewith. Gradual filing of the mixing chamber throughout the day maximises the cultivation of the bacteria from its dormant, supplied state to an active state ready for dispensing. This enables said bacteria to only be activated onsite in the mixing chamber, immediately before use. This greatly improves the shelf life, performance and transportability of said bacteria.

A pressure regulator is, preferably, located upstream of the first Venturi means to, in use, ensure fluid is supplied to the system at the desired pressure. A double check valve is, advantageously, located upstream of the first Venturi means. Furthermore, a Eurogap certified backflow prevention device is preferably associated with the conduit to further protect the water supply from contamination or pollution. Advantageously, a casing formed by rotomoulding houses all the apparatus. Further advantageously a casing formed by rotomoulding houses all the apparatus apart from the mixing chamber.

It is preferable that the present invention operates on a low powered timer to control the times at which the first or the first and second timer operated valves operate and thus when mixing and dispensing of bacteria occurs. The device is, therefore, preferably able to run on batteries or draw little power from a mains supply.

According to a second aspect of the invention, there is provided a method of introducing nutrient and bacteria into a conduit for mixing therein, comprising the steps of:

a) providing a conduit with an upstream and a downstream section, the downstream section of the conduit comprising a first Venturi eductor means with at least two inlet ports, wherein the at least two inlet ports of the first Venturi eductor means are in fluid communication with a supply of nutrient and bacteria respectively, b) passing a fluid along the conduit such that a pressure drop in the first Venturi eductor means draws nutrient and bacteria into said eductor to mix therein; and c) allowing the bacteria in said mixture to cultivate for a predetermined period of time.

Preferably, the method of introducing nutrient and bacteria into a conduit for mixing therein further comprises the steps of:

d) repeating steps (b) and (c) above until a desired amount of bacteria is cultivated; and e) dispensing the fluid to a use location.

According to a third aspect of the present invention, there is provided a method of cultivating bacteria, comprising the steps of:

a) providing an apparatus according to the present invention, b) passing a fluid along the conduit;

c) allowing the fluid to cultivate for a predetermined period of time;

d) repeating the previous two steps until a desired amount of fluid is cultivated; and e) dispensing the fluid to a use location.

Preferably, the step of passing fluid along the conduit is achieved by programming the first timer operated valve to automatically open and close. Further advantageously, this step and the step of allowing the fluid to cultivate for a period of time can automatically be repeated by programming said first timer operated valve. The step of dispensing the fluid to a use location may be achieved by the use of the inverted U shaped conduit which siphons fluid therealong when a certain fluid height is reached in the mixing chamber, or by programming the second timer operated valve.

The apparatus is preferably a waste material treatment apparatus and a preferred use of the present invention is in the cultivation and dispensing of bacteria capable of breaking down fats, oils and greases typically found deposited in the plumbing and grease traps associated with sinks of commercial kitchens. The apparatus could also be used to clean fats, oils and greases from the plumbing associated with industrial sites such as those concerning food processing or the like.

The steps of passing fluid along the conduit, allowing said fluid to cultivate and discharging said fluid to a use location, form one cycle. One or more cycles can be performed at regular intervals throughout a 24 hour period. This, for example, enables a user to cultivate a new batch of active bacteria in the fluid whilst the kitchen is being used and then dispense said batch after the kitchen is closed so it has time to act without being washed away by a further flow of wastewater. A similar approach could be used to clean plumbing associated with food processing sites or the like overnight or during a typically low period of activity.

Advantageously, step (b) is performed for 20 to 30 seconds. More specifically step (b) is, preferably, performed for 27 seconds. The time step (b) is performed for may depend on the pressure of the fluid passed along the conduit.

Advantageously, step (d) is performed for 1 to 3 seconds. More specifically step (d) is, preferably, performed for 1 second. The time step (d) is performed for may depend on the pressure of the fluid passed along the conduit.

Preferably, a desired amount of fluid is contained in the mixing chamber of the present invention by performing steps (b) and (c) six times, and, it is also preferable that step (e) is performed for 10 seconds. 3.5 litres of fluid is, preferably, added to the mixing chamber before dispensing and it is also preferable that 1 litre of fluid is retained in the mixing chamber after dispensing to a use location.

It will be apparent to those skilled in the art that the present invention has many different uses in addition to that discussed above and it will also be apparent that in order to add nutrient and bacteria two Venturi eductors, each with one inlet port, could be used instead of one with two inlet ports. By varying the number of Venturi eductors connected in series or in parallel and also the number and type of fluids attached thereto the present invention could be used in any application whereby the automated mixing of more the one fluid for dispensing is required. The hands-free operation of the device enables it to be used with toxic substances that would be harmful if touched, inhaled, or the like or fluids that must remain sterile, such as those used in the production of food and medicines, etc. It will also be apparent that any number of Venturi eductors could be used in conjunction with any number of mixing chambers or that no mixing chamber could be used and the nutrient and bacteria could simply mix in the conduit of the apparatus. Similarly, a single Venturi eductor with three inlet ports could be used to draw in bacteria, nutrient and a third fluid for mixing therein.

In order that the invention may be well understood, there will now be described an embodiment thereof, given by way of example, reference being made to the accompanying drawings, in which.

FIGS. 3(a), (b) and (c) are cross-sectional views of the apparatus according to the present invention showing the mixing chamber before filling for the first time, after filling and after dispensing.

Figure 1:
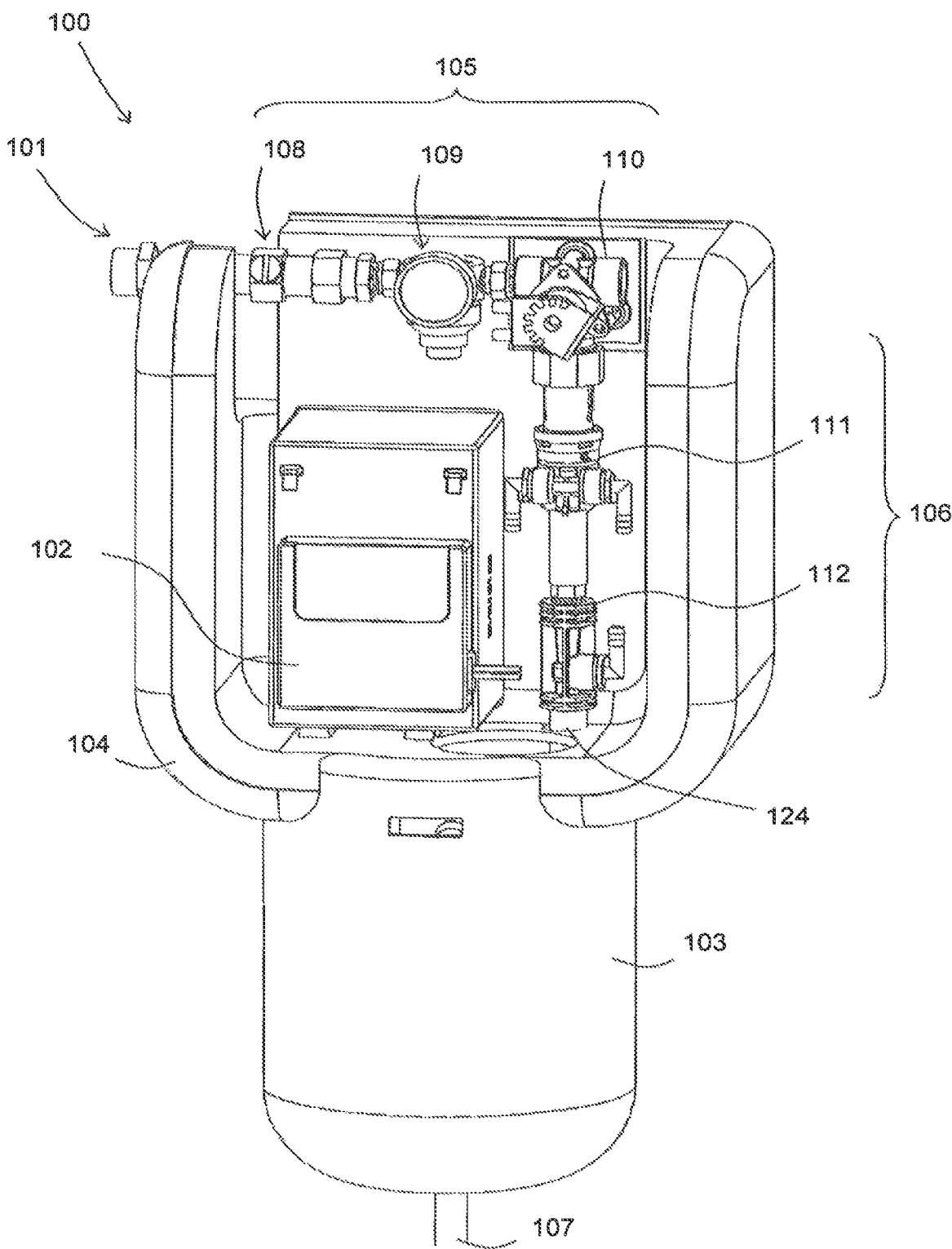
FIG. 1 is a front view of an apparatus according to the invention with a cover of a casing removed, showing articles contained therein.

Referring firstly to FIG. 1, there is shown a bacteria cultivating and dispensing unit 100 that, in use, mounts on the wall of a commercial kitchen above the sink.

For the purposes of the description herein, "top", "bottom", "left" and "right" and derivatives thereof shall be related to the invention as oriented in FIG. 1 as if the unit 100 were wall mounted. However, it is to be understood that the invention may assume various other orientations, except where expressly specified to the contrary.

The unit 100 comprises a conduit 101, a battery-powered timer 102 and a mixing chamber 103. The conduit 101 and timer 102 are housed in a wall mounted, rotomoulded casing 104 substantially cuboid in shape and the mixing chamber 103 is secured externally and to the bottom of said casing 104 and in fluid communication with the conduit 101. To comply with local water regulations an air gap is provided between the conduit 101 and the mixing chamber 103.

Figure 2:
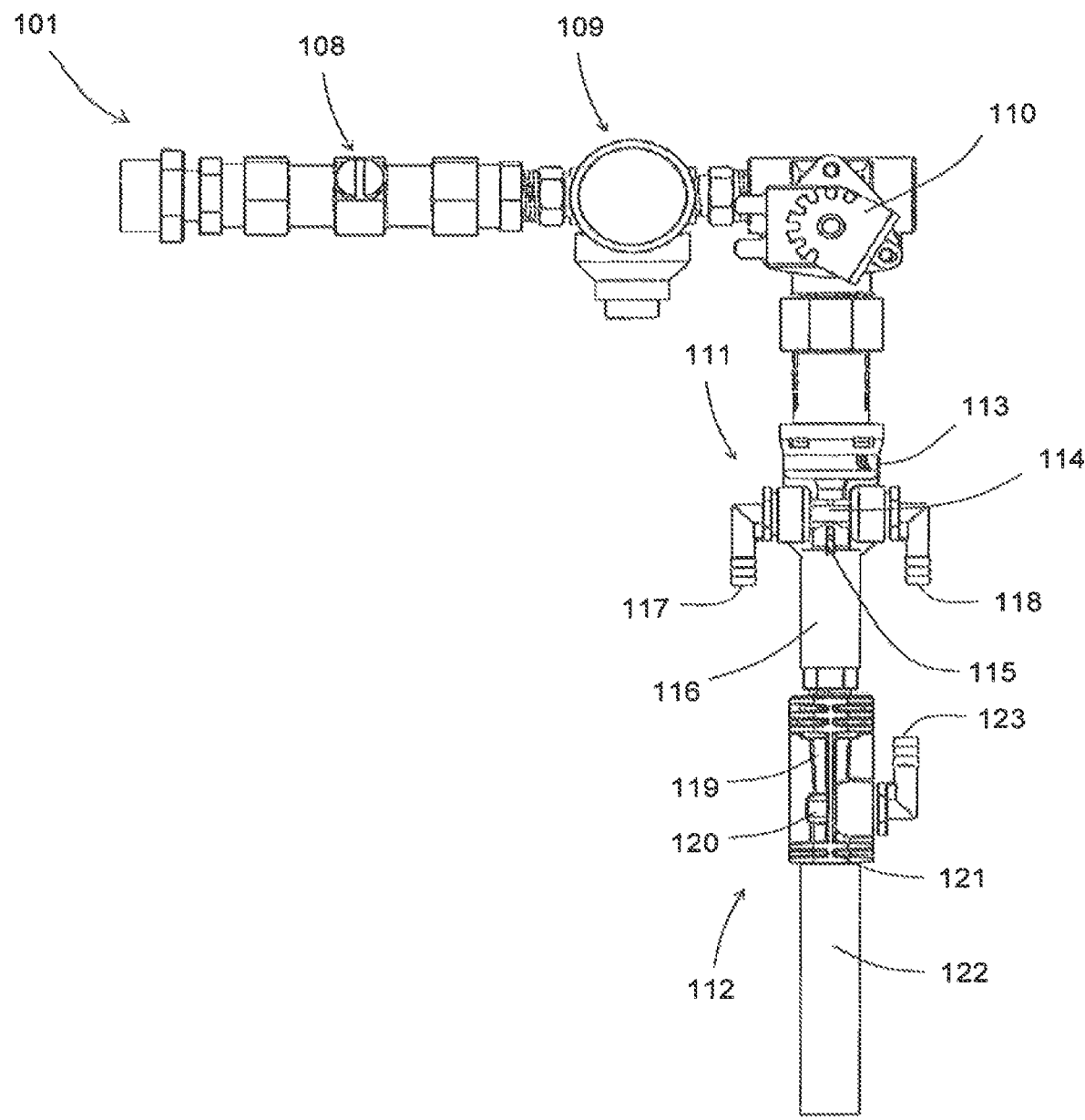
FIG. 2 is a detailed view of a conduit of FIG. 1.

The conduit 101 is shown in more detail in FIG. 2 and is of the form of an inverted L shape, comprising a horizontal section 105 which enters the casing at the top left corner and runs to the top right corner and a vertical section 106 which runs from the top right corner to the bottom right. This arrangement optimises the size of the casing 104 by allowing room in the bottom left corner of the casing 104 for the timer 102.

The conduit 101 is, in use, connected to a mains water supply (not shown) such that water enters said conduit 101 at the end positioned at the top left corner of the casing 104 and proceeds through the conduit 101 to be discharged into the mixing chamber 103 via the end of the conduit 101 positioned at the bottom right corner of the casing 104. An outlet port 107 extends from the bottom of the mixing chamber 103 and, in use, is connected to the drainage pipe of a commercial kitchen sink (not shown) at a position upstream of a grease trap.

Connected in series from left to right along the horizontal section 105 of the conduit 101 is a double check valve 108, pressure regulator 109 and solenoid valve 110 and connected in series from top to bottom along the length of the vertical section 106 of the conduit 101 is a first Venturi eductor means 111 comprising a single Venturi followed by a second Venturi eductor means 112 also comprising a single Venturi.

The first Venturi eductor 111 has an outwardly cylindrical housing and contains an axially symmetric chamber running its length. This chamber is in four successive sections from top to bottom as shown; a first section 113, a second section 114, a third section 115 and a fourth section 116.

The first section 113 comprises an inwardly tapering frusto-conical inlet and the second section 114 comprises a narrow parallel-sided duct with two inlets located either side and in fluid communication with said duct. The inlet shown on the left hand side is known as the bacteria inlet 117 and, in use, is connected to a supply of dormant starter bacteria in liquid form. The inlet shown on the right hand side is known as the nutrient inlet 118 and, in use, is connected to a supply of bacteria nutrient, also in liquid form. The composition of the bacteria and nutrient is known in the art and therefore will not be described in more detail.

In use, water enters the first Venturi eductor 111 through the inwardly tapering frusto-conical inlet of the first section 113. The water then accelerates as the first section 113 narrows causing its pressure to drop. This lower pressure water then enters the parallel-sided second section 114 and the pressure differential between the water passing therethrough and the liquid bacteria and nutrient in fluid communication with said second section 114 draws said bacteria and nutrient into the second section 114 to mix with the water in the duct.

The chamber then opens out into the frusto-conical third section 115 which smoothly disperses and decelerates the water, nutrient and bacteria mix into the fourth section 116 which is a parallel-sided duct of the same diameter cross section as the mouth of the first section 113.

The second Venturi eductor 112 is of the same form as the first, with a narrowing, frusto-conical first section 119, a parallel-sided second section 120, a widening frusto-conical third section 121 and a parallel-sided fourth section 122. However, the duct of the second section 120 has only one inlet. This inlet is known as the air inlet 123.

In use, the water, nutrient and bacteria mix accelerates through the first section 119 of the second Venturi eductor 112 such that, in the same way as with the first Venturi eductor 111, the mix is of a lower pressure when passing through the second section 120. As the air pressure within the second section 120 of the second Venturi eductor 112 drops, the higher pressure air of the surrounding atmosphere is drawn into said second section 120 to mix with the water, nutrient and bacteria passing therethrough. The second Venturi 112 is thus acting as an aspirator. In order to prevent foreign objects being introduced to the system at this point, the air inlet 123 of the second Venturi eductor 112 is covered by a mesh filter (not shown).

As with the first Venturi eductor 111, the chamber of the second Venturi eductor 112 then opens out into the frusto-conical third section 121 which smoothly disperses and decelerates the water, nutrient, bacteria and air mix into the parallel-sided fourth section 122. This mix is then, in turn, discharged into the mixing chamber 103.

The mixing chamber 103 is cylindrical in shape and has a capacity in the range of approximately 3.5 to 6 litres. In use, the conduit 101 discharges the water, bacteria, nutrient and air mix into the mixing chamber 103 at the top right corner via an inlet port 124. As mentioned previously, an outlet port 107 extends from the bottom of the mixing chamber 103. This is in fluid communication with the drainage pipe of a commercial kitchen sink.

A discharge pipe 125 is housed inside the mixing chamber 103. This pipe 125 is connected at one end to the outlet port 107 and is free at its other end. The discharge pipe 125 is of the form of an inverted U shape with the free end providing an inlet for the contents of the mixing chamber 103. The free, or inlet end of the discharge pipe 125 is positioned above the outlet port 107 such that the vertical distance between the inlet end of the discharge pipe 125 and the outlet port 107 defines a height of fluid mixture in the mixing chamber 103 that cannot flow along the discharge pipe 125 and thus out of the mixing chamber 103. The volume of this remaining fluid mixture is 1 litre.

The discharge of the fluid mixture in the mixing chamber 103 is governed by the level of said fluid mixture in said chamber rising above the apex of the inverted U shaped discharge pipe 125 to thus siphon up said pipe 125 and flow out of the mixing chamber 103. The vertical height of the pipe 125 from inlet end to the apex of the inverted U shape, together with the volume of the mixing chamber 103, thus determines the volume of fluid mixture to be discharged.

Operation of the unit 100 is automatic and governed by the timer 102. The timer 102 is battery-powered and is supplied un-programmed. Upon installation of the unit 100 the timer 102 is programmed by an installer to open and close the solenoid valve 110 at certain times throughout the day. Opening the solenoid valve 110 enables water to enter the vertical section 106 of the conduit 101 and thus pass through the first and second Venturi eductors 111, 112 respectively, drawing bacteria, nutrient and air as previously described and then discharging this fluid mixture into the mixing chamber 103 when the level of fluid mixture is high enough to siphon along the pipe 125. As such the contents of the mixing chamber 103 are automatically discharged down the discharge pipe 125 to enter the drainage pipe of the commercial kitchen sink upstream of the grease trap.

The above description discloses a first embodiment of the invention. In a second embodiment of the invention a pipe 125 is not required and the discharge of the mixing chamber is governed by a second valve located at the outlet port 107. The second valve (not shown in the figures) is controlled by the timer 102. The timer 102 is pre-programmed to open and close said second valve in order to discharge fluid from the mixing chamber 103 via the outlet port 107.

In either embodiment the timer is pre-programmed to run the following cycle over a 24 hour period:

| Fill No. | Time of Day | Length of time valve is opened for: |
| --- | --- | --- |
| 1 | 02:10 | 27 seconds - Main fill |
| 2 | 05:00 | 1 second - Aeration charge |
| 3 | 07:00 | 1 second - Aeration charge |
| 4 | 10:00 | 1 second - Aeration charge |
| 5 | 14:00 | 1 second - Aeration charge |
| 6 | 18:00 | 1 second - Aeration charge |
| 7 | 22:00 | 1 second - Aeration charge |
| 8 | 02:00 | 10 seconds - Flush. Injects the active bacteria |

In the second embodiment the flush step occurs when the timer 102 opens the second valve, whereas in the first embodiment the flush step happens automatically when the level of fluid mixture in the mixing chamber 103 is high enough to siphon along the pipe 125

Figure 3:
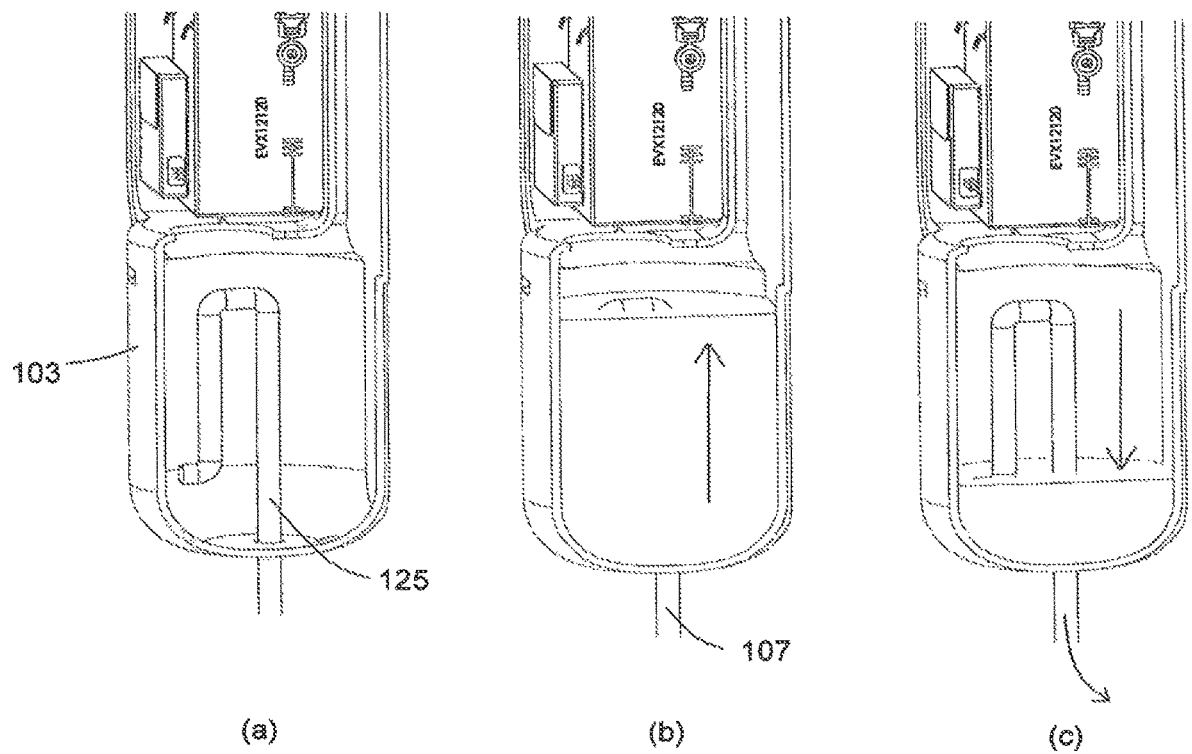

The filling and discharging cycle shown in the above table is illustrated in FIGS. 3(*a*), (*b*) and (*c*). The cycle allows for the bacteria, nutrient, water and air mix in the mixing chamber 103 to cultivate over a 24 hour period in order that the dormant bacteria supplied to the system can incubate and grow into active bacteria suitable for breaking down organic material such as fats, oils and greases. The regular aerating of the mixture throughout the cycle also aids this incubation process until the desired amount of active bacteria is contained in the mixing chamber 103 ready to be flushed.

It will be apparent that the apparatus as herein described could be used with many different strengths, concentration and types, etc, of bacteria and nutrient and thus the timings listed above could be altered to optimise operation of the apparatus given such changes. Furthermore, the time of day of the discharge of active bacteria from the apparatus could be varied in order to maximise the length of time that said bacteria can act on any fats, oils and greases without being washed away by further wastewater. The apparatus could also be programmed to run more than one cycle in a 24 hour period.

It will also be appreciated that the volume of the mixing chamber 103 could be altered depending on user requirements. A bubbler could be added to the mixing chamber 103 to further aid in aerating the water, bacteria, nutrient and air mix and, finally, a heating element could be added to said mixing chamber 103 to aid growth of the active bacteria.

The present invention is not limited to the specific embodiments described above. Alternative arrangements will be apparent to a reader skilled in the art.

The invention claimed is:

1. A method of removing grease from grease traps cultivating bacteria, comprising the steps of:
   a) cultivating bacteria through the steps of:
      i) providing a conduit with an upstream section and a downstream section and a mixing chamber into which the conduit discharges,
      wherein the upstream section of the conduit comprises an inlet in fluid communication with a source of water and a first valve associated with the conduit, said first valve controlling a supply of water along said conduit from the inlet; the downstream section of the conduit comprising a first Venturi eductor with at least two inlet ports, wherein one of said inlet ports is in fluid communication with a supply of nutrient and another of said inlet ports is in fluid communication with a supply of dormant bacteria suspended in liquid respectively,
      wherein the method further comprises the step of employing a second Venturi eductor in fluid communication with the first Venturi eductor and connected in series between the first Venturi eductor and the mixing chamber,
      ii) passing water along the conduit such that a pressure drop in the first Venturi eductor draws the nutrient and the dormant bacteria suspended in liquid into said eductor to discharge into the mixing chamber and mix therein;
      iii) allowing the dormant bacteria suspended in liquid in said mixing chamber to cultivate for a predetermined period of time;
      iv) repeating steps (ii) and (iii) until a desired amount of the dormant bacteria suspended in liquid is cultivated; and
   b) dispensing the cultivated bacteria into the drainage pipe of the commercial kitchen via an outlet port present in the mixing chamber,
   wherein said second Venturi eductor having at least one inlet port, wherein the at least one inlet port of the second Venturi eductor is in fluid communication with a supply of air such that, in use, air is drawn into said second Venturi eductor by the water, nutrient and bacteria mix passing from the first Venturi educator in to the second Venturi educator and wherein the air supplied to the system is drawn from the atmosphere.

2. The method according to claim 1, wherein each of the method steps are initiated automatically and governed by a battery powered timer programmed to open and close a solenoid valve at certain times throughout a 24 hour period, and
   wherein opening the solenoid valve enables water to pass through the conduit and into the first and second Venturi eductors respectively, drawing bacteria, nutrient and air and then discharging this fluid mixture into a mixing chamber.

3. The method according to claim 2, further comprising the step of employing a second valve, said second valve associated with the outlet port of the mixing chamber such that the opening and closing of the outlet port is controlled by the second valve.

4. The method according to claim 3, wherein the second valve is a timer operated valve programmed to operate automatically at pre-set intervals.

5. The method according to claim 4, wherein the first and second valves are programmed to enable the step of
   a) a main fill of the mixing chamber,
   b) an aeration charge of the mixing chamber, and
   c) flushing of the content of the mixing chamber to the use location.

6. The method according to claim 4, wherein the bacteria, nutrient, water and air mix in the mixing chamber to cultivate over a 24 hour period and regular aerating of the mixture occurs throughout that 24 hour period.

7. The method according to claim 2, further comprising the step of retaining at least 1 litre of fluid in the mixing chamber.

* * * * *